United States Patent [19]

Patterson et al.

[11] 4,237,070

[45] Dec. 2, 1980

[54] NOVEL PROCESS FOR PREPARING ANILINE BY CATALYTIC REACTION OF VINYL CYCLOHEXENE AND NITROBENZENE

[75] Inventors: John A. Patterson, Fishkill, N.Y.; Wheeler C. Crawford, Houston; James R. Wilson, Missouri City, both of Tex.

[73] Assignee: Texaco Inc., White Plains, N.Y.

[21] Appl. No.: 944,041

[22] Filed: Sep. 20, 1978

[51] Int. Cl.$^3$ .............................................. C07C 85/11
[52] U.S. Cl. .................................. 260/580; 252/470; 252/474; 260/283; 260/465 E; 260/563 R; 260/563 C; 260/570.8 R; 260/570.9; 260/575; 260/583 M; 560/103; 585/433; 585/434; 585/444
[58] Field of Search ............... 260/580, 668 D, 669 R, 260/583 M, 563 R; 252/470, 474, 447

[56] References Cited

U.S. PATENT DOCUMENTS

| B 430,157 | 2/1976 | Juguin et al. ................... 260/668 D |
| 2,799,708 | 7/1957 | Oakley et al. ................... 252/447 X |
| 2,998,377 | 8/1961 | Beuther et al. ................. 252/470 X |
| 3,123,574 | 3/1964 | Zajcew ................................ 252/447 |
| 3,156,735 | 11/1964 | Armstrong ................. 260/668 D X |
| 3,218,268 | 11/1965 | Arnold ............................ 252/474 X |
| 3,325,504 | 6/1967 | Grasselli ....................... 252/470 X |
| 3,354,212 | 11/1967 | Donaruma ...................... 260/580 X |
| 3,449,063 | 6/1969 | Griffing et al. ................ 252/474 X |
| 3,646,127 | 2/1972 | Akiyama et al. .............. 252/470 X |
| 3,655,747 | 4/1972 | Sennewald et al. ........... 252/474 X |
| 3,674,884 | 7/1972 | Moritani et al. .............. 260/669 R |
| 3,904,371 | 9/1975 | Neti et al. ..................... 252/447 X |
| 4,107,204 | 8/1978 | Murib ............................ 252/447 X |

FOREIGN PATENT DOCUMENTS

| 45-490 | 1/1970 | Japan ........................................ 260/580 |
| 1510195 | 5/1978 | United Kingdom ................... 252/474 |
| 281455 | 12/1970 | U.S.S.R. .................................. 260/580 |

OTHER PUBLICATIONS

Kozlov et al., "Chem. Ab.", vol. 65, Ab. No. 18451$^h$, (1966).

Primary Examiner—John Doll
Attorney, Agent, or Firm—Carl G. Ries; Robert A. Kulason; Carl G. Seutter

[57] ABSTRACT

A nitrohydrocarbon, typified by nitrobenzene, is reacted with a hydrocarbon such as 4-vinyl-1-cyclohexene at 70° C.–360° C. and 0–500 psig to give product stream containing aniline, ethylbenzene, and styrene; heterogeneous catalyst contains Group VIII noble metal, Group I B metal and optionally Group VI B metal, typically 0.5% platinum and 5% cuprous oxide on gamma alumina.

18 Claims, 1 Drawing Figure

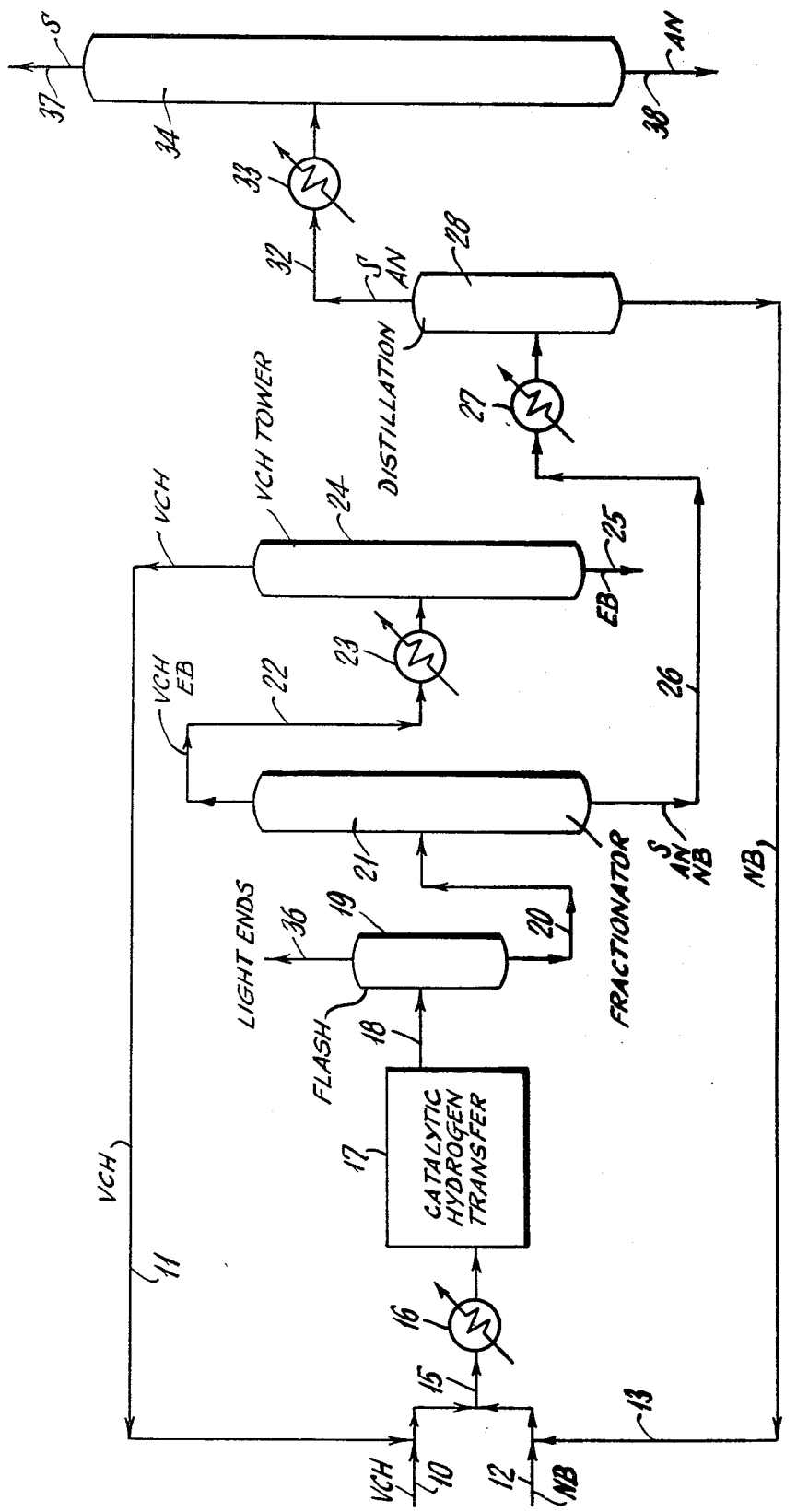

NOVEL PROCESS FOR PREPARING ANILINE BY CATALYTIC REACTION OF VINYL CYCLOHEXENE AND NITROBENZENE

FIELD OF THE INVENTION

This invention relates to reaction of a nitrohydrocarbon with a hydrocarbon such as 4-vinyl-1 cyclohexene to prepare amine products such as aniline. More particularly it relates to the use of a catalyst to effect such conversions.

BACKGROUND OF THE INVENTION

As is well known to those skilled in the art, nitro-compounds such as nitrobenzene may be reduced to amines such as aniline. The decreased use of butadiene in rubber compositions results in over-supply of this material; and this may be converted (by well-known dimerization processes) to vinyl cyclohexene.

It is known (Bin Din et al. Synthesis 1978 pages 23-24) that nitro compounds may be reduced to amines in the presence of hot liquid paraffin at 360° C.–390° C.

SUMMARY OF THE INVENTION

In accordance with certain of its aspects, the novel method of this invention may comprise passing a charge stream containing vinyl cyclohexene and $R'NO_2$, wherein $R'$ is alkyl, cycloalkyl, aryl, aralkyl, or alkaryl, into contact at hydrogen transfer conditions with a supported catalyst bearing (i) a Group VIII noble metal and, per mole of Group VIII noble metal, (ii) 1–20 moles of Group I B metal, present as oxide, and (iii) 0–20 moles of Group VI B metal present as oxide, thereby forming a product stream containing $R'NH_2$; and recovering said product stream containing $R'NH_2$.

DESCRIPTION OF THE INVENTION

Charge hydrocarbon to the process of this invention is vinyl cyclohexene. 4-vinyl-1-cyclohexene, sometimes referred to as "butadiene dimer," may be commercially available or it may be prepared by dimerization of butadiene by well known processes typified by that set forth at U.S. Pat. No. 2,544,808 to A. E. Staley, or *The Chemistry of Petrochemicals* by M. J. Astle (1956) page 123. Although the process of this invention may be employed to convert 2-vinyl-1-cyclohexene or 3-vinyl-1-cyclohexene to desired products, it is found that the advantages of this process may be more readily attained using, as charge, the 4-vinyl-1-cyclohexene isomer.

The charge vinyl cyclohexene may be used as recovered in impure or crude form or it may be purified. Preferably it will be free of any added stabilizers.

The process of this invention may be carried out by reacting the vinyl cyclohexene with a nitrohydrocarbon $R'NO_2$ wherein $R'$ is a hydrocarbon moiety selected from the group consisting of alkyl, cycloalkyl, alkaryl, aryl and aralkyl.

Although it may be possible to utilize polynitro compounds such as dinitrobenzene etc. and such compounds are included in the representation $R'NO_2$, it is more preferred to use a mononitro compound.

In the above compound, $R'$ may be a hydrocarbon radical selected from the group consisting of alkyl, cycloalkyl, aralkyl, aryl, and alkaryl including such radicals when inertly substituted. When $R'$ is alkyl, it may typically be propyl, butyl, i-butyl, hexyls, octyls, etc. When $R'$ is cycloalkyl, it may typically be cyclohexyl, etc. When $R'$ is aralkyl, it may typically be benzyl, etc. When $R'$ is aryl, it may typically be phenyl, naphthyl, etc. When $R'$ is alkaryl, it may typically be tolyl, xylyl, etc. $R'$ may be inertly substituted i.e. it may bear a non-reactive substituent such as alkyl, aryl, cycloalkyl, ether, halogen, nitro, etc. Typically inertly substituted $R'$ groups may include p-chlorophenyl, 3-chloro-5-methylphenyl, etc. The preferred $R'$ groups may be aryl. $R'$ may preferably be phenyl.

Illustrative compounds $R'NO_2$ may include:

TABLE nitrobenzene
dinitrobenzene
p-nitrotoluene
2,4-dinitrotoluene
p-nitrochlorobenzene
1-nitropropane
p-nitroanisole
1-nitro-n-octane
3-nitrophenol
nitrocyclohexane
1,2-dinitroaniline
6-nitroquinoline
4-nitrobenzonitrile
methyl 4-nitrobenzoate The most preferred of these compounds is nitrobenzene.

In practice of the process of this invention, vinyl cyclohexene is reacted with $R'NO_2$, in the presence of a hydrogen transfer catalyst at hydrogen transfer conditions. Hydrogen transfer catalysts are characterized by the ability of the catalyst system to exchange hydrogen between two molecules of different polarity. The catalysts are heterogeneous catalysts.

In practice of the process of this invention according to certain of its aspects, vinyl cyclohexene is reacted with nitrohydrocarbon $R'NO_2$ in the presence of a supported catalyst bearing (i) a Group VIII noble metal, and, per mole of Group VIII noble metal, (ii) 1–20 moles of Group I B metal, present as oxide, and (iii) 0–20 moles of Group VI B metal present as oxide.

The Group VIII noble metal may include ruthenium Ru, rhodium Rh, palladium Pd, osmium Os, iridium Ir, or platinum Pt. Platinum and palladium may be preferred; and platinum is most preferred.

The Group I B metal may include copper Cu, silver Ag, and gold Au. The preferred metal is copper. It is preferred that the metal be in a lower valence state. Thus although it is possible to utilize copper as CuO or $CuO_2$, the preferred oxide is $Cu_2O$. ($Cu_4O$ may be present). Gold may be present as $Au_2O_3$, but more preferably as $Au_2O$. Silver may be present as AgO (sometimes referred to as $Ag_2O_2$) but more preferably as $Ag_2O$.

The Group VI B metal may include chromium Cr, molybdenum Mo, or tungsten, W. The preferred of these metals may be chromium, present as oxide $Cr_2O_3$.

Although the Group I B metal and the Group VI B metal are said to be present as oxides, the latter may be in fact be in a combined state as eg in copper chromate, copper tungstate, copper molybdate, etc.

The support, on which the other catalyst compounds are deposited may include active, inactive, or inert materials such as alumina, silica, silica-alumina, diatomaceous earth, zeolites, etc. The preferred support may be alumina, preferably gamma alumina. The support may be in the form of pellets, extruded shapes including cylinders, spheres, or random shapes. A typical support may be 5 mm (l)×5 mm (d) alumina cylinders.

The product supported catalyst may contain the several components in amount, as shown in moles in the following table:

TABLE I

| Component | Broad | Preferred | Typical |
| --- | --- | --- | --- |
| (VIII) | 0.2–100 | 0.4–20 | 1 |
| (I B) | 0.2–2000 | 0.4–400 | 7 |
| (VI B) | 0–2000 | 0–400 | 7 |

In the typical composition, this means that the Group VIII noble metal is present in the form of the metal in amount of 1 molar parts of metal. The Group I B metal is present as its oxide, in amount of 7 molar parts of the metal oxide. The Group VI B metal is present as its oxide, in amount of 7 molar parts of the metal oxide. It will be apparent to those skilled in the art that although the Groups IB and VI B are reported as oxide, they may in fact be present in other compositions eg copper chromate.

In the preferred embodiment wherein the Group VIII noble metal may be platinum, the Group I B metal copper, and the Group VI B metal is chromium, the molar parts may be:

TABLE II

| Component | Broad | Preferred | Typical |
| --- | --- | --- | --- |
| Platinum | 0.2–100 | 0.4–20 | 1 |
| Copper | 0.2–2000 | 0.4–400 | 7 |
| Chrominum | 0–2000 | 0–400 | 7 |

The supported catalyst may contain the metals, as indicated in total amount of 1%–25 %, preferably 2%–15%, say 11% by weight of support. A catalyst bearing the designation 0.5% Pt: 5% $Cu_2O:Al_2O_3$ may be found to contain 100 parts of alumina and 0.5 parts of the metal platinum and 5 parts of cuprous oxide; the latter may be present e.g. as copper aluminate.

Preferred catalysts may contain (i) $Pt-Cu_2O-Al_2O_3$; (ii) $Pt-Cu_2O - Cr_2O_3 - Al_2O_3$; (iii) $Pd-Cu_2O - Al_2O_3$; (iv) $Pd-Cu_2O - Cr_2O_3 - Al_2O_3$; (v) $Pt-Cu_2O-Cr_2O_3 - Al_2O_3$. Specific preferred catalysts may include those set forth in the following table:

TABLE III

| (A) | 0.5% | Pt |
| --- | --- | --- |
|     | 5%   | $Cu_2O$ |
|     |      | $Al_2O_3$ |
| (B) | 1%   | Pt |
|     | 5%   | $Cu_2O$ |
|     | 5.3% | $Cr_2O_3$ |
|     |      | $Al_2O_3$ |
| (C) | 1%   | Pd |
|     | 5%   | $Cu_2O$ |
|     |      | $Al_2O_3$ |
| (D) | 1%   | Pd |
|     | 5%   | $Cu_2O$ |
|     | 5.3% | $Cr_2O_3$ |
|     |      | $Al_2O_3$ |
| (E) | 0.5% | Pt |
|     | 5%   | $Cu_2O$ |
|     | 5.3% | $Cr_2O_3$ |
|     |      | $Al_2O_3$ |

The catalyst may be prepared by impregnating catalyst support with solutions (preferably aqueous) containing the metals. It may be possible to deposit the metals from one solution containing all of the metals; it is however preferred to deposit each metal separately from its solution. It is preferred that the Group I B metal be deposited first, then (when present) the Group VI B metal, and lastly the Group VIII noble metal. In the preferred embodiment, after each metal is deposited on the support, it is dried and calcined prior to further deposition. After the last metal, preferably the Group VIII metal is deposited, dried, and calcined, it is preferably reduced in flowing hydrogen.

In the preferred embodiment, 50–500 parts, preferably 80–120 parts, say 100 parts of catalyst support may be immersed in solution containing 1–25 parts, preferably 4–20 parts, say 10 parts of a soluble compound of a Group I B metal. Typically this compound may be copper nitrate, copper acetate, copper oxalate, etc. silver acetate, silver nitrate, silver oxalate, silver tartrate, etc; nitroauric acid, gold chloride etc. The metal may be in a higher or a lower valence state. Preferred may be copper nitrate. The copper may be as cupric or more preferably as cuprous copper.

The catalyst support may remain in contact with the solution for 1–4 hours, preferably 1–2 hours, say 1.5 hours at 10°–50° C. preferably 20°–30 ° C., say 25° C. The support particles which absorb solution during this period, may be separated and dried at 100°–140° C., preferably 105° C.-115° C., say 110° C. for 4–24 hours, preferably 6–10 hours, say 8 hours. The catalyst particles may be calcined at 370°–550° C., preferably 450°–500° C., say 480° C. for 1–4 hours, preferably 2–3 hours, say 2 hours.

The catalyst may then be cooled to 10° C.–40° C., preferably 20° C.–30° C., say 25° C. and then contacted with 2–50 parts, say 40 parts of solution containing 1–25 parts, say 10 parts of a soluble salt of a metal of Group VI B of the Periodic Table. Illustrative soluble salts may include ammonium chromate, ammonium molybdate, ammonium tungstate, etc. Preferred may be ammonium chromate.

The catalyst support may be allowed to stand in contact with this solution for 0.5–3, preferably 1–2, say 1.5 hours, with mixing at 10°–40° C., preferably 20°–30° C., say 25° C. At the end of this time, the catalyst support may be found to have absorbed a substantial portion of the solution. The supernatant liquid may be poured off and the resultant catalyst particles may be dried in an oven for 4–24 hours, preferably 6–10 hours, say 8 hours at 95°–150° C., preferably 110°–120° C., say 120° C. The loaded catalyst particles may be calcined at 370°–550° C., preferably 450°–500° C., say 480° C. for 1–4 hours, preferably 2–3 hours, say 2 hours.

Clearly if the catalyst is not intended to contain Group VI B metal, this step will be omitted.

The catalyst support, now loaded with Group I B metal, and optionally Group VI B metal, may be loaded with Group VIII noble metal by immersing in 500 parts of solution contain 0.1–10 parts, preferably 0.3–0.7, say 5 parts of a soluble compound of the Group VIII noble metal. Typically this compound may be a salt such as chloroplatinic acid, palladium dichloride, iridium dichloride, rhodium trinitrate, osmium dichloride, ruthenium trichloride, etc. Preferred is a solution of chloroplatinic acid (containing 40% platinum).

The catalyst support may be allowed to stand in contact with this solution for 0.5–3, preferably 1–2, say 1.5 hours, with mixing at 10°–40° C., preferably 20°–30° C., say 25° C. At the end of this time, the catalyst support may be found to have absorbed a substantial portion of the solution. The supernatant liquid may be poured off and the resultant catalyst particles may be dried in an oven for 4-24 hours, preferably 6-10 hours, say 8 hours at 95°-150° C., preferably 110°-120° C., say 120° C. The loaded catalyst particles may be calcined at 370°-550° C., preferably 450°-500° C., say 480° C. for 1-4 hours, preferably 2-3 hours, say 2 hours.

Preferably the so-obtained catalyst is treated by contact with flowing hydrogen (VHSV at STP of 0.1-10 preferably 1-5, say 2) at 50° C.-300° C., preferably 75° C.-200° C., say 150° C. for 1-10 hours, say 2 hours at atmospheric pressure. During this pretreatment, the Group VIII noble metal may be substantially reduced to free metal and the Group I B metal may be reduced to a lower valence state and/or to free metal.

The catalyst compositions so-prepared are ready for use in the process of this invention.

Reaction of vinyl cyclohexene and nitro compound R'NO$_2$ may be effected by passing substantially equimolar amounts of each in liquid phase through a bed of catalyst. The reaction conditions may be as follows for a continuous reaction:

TABLE IV

| Condition | Broad | Preferred | Typical |
|---|---|---|---|
| Temperature °C. | 70-360 | 170-320 | 260 |
| Pressure psig | 0-500 | 0-100 | 50 |
| LHSV | 0.003-6 | 0.006-2 | 1.5 |

The hydrogen transfer reaction conditions for batch reaction may include:

TABLE

| Condition | Broad | Preferred | Typical |
|---|---|---|---|
| Temperature °C. | 170-360 | 170-250 | 200 |
| Pressure psig | 0-500 | 0-100 | 50 |
| Time of Reaction hr | 1-20 | 2-15 | 10 |
| Mole ratio of R'NO$_2$ to vinyl cyclohexene | 0.1-1 | 0.3-0.7 | 0.67 |
| Mole ratio of catalyst* to vinyl cyclohexene | 0.0001-0.5 | 0.002-0.05 | 0.02 |

*active components

The reaction is typically carried out in liquid phase under autogeneous pressure in the presence of the heterogeneous catalysts.

During the course of the typical reaction, in liquid phase, hydrogen transfer occurs, the vinyl cyclohexene being dehydrogenated to produce styrene and ethylbenzene; and nitrobenzene being reduced to aniline:

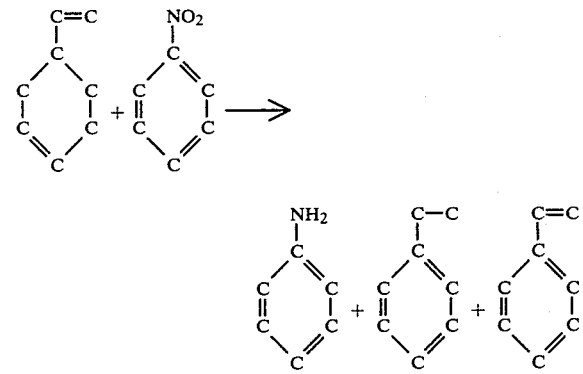

It may be desirable to carry out the reaction in the presence of a diluent-solvent which does not react under the conditions of reaction and such diluent-solvents may include hydrocarbons, preferably aromatic hydrocarbons such as benzene, xylene, toluene, etc., preferably benzene.

Reactor effluent may be characterized (in a preferred embodiment) by the presence of product ethylbenzene (EB), styrene (S), and aniline (AN) and also unreacted charge vinyl cyclohexene (VCH) and nitrobenzene (NB). Typically the selectivities (in mole %) may be as follows:

TABLE

| Selectivity | Broad | Typical |
|---|---|---|
| EB | 5-40 | 16 |
| S | 1-15 | 10 |
| AN | 5-50 | 25 |

It will be clear to those skilled in the art, that the selectivity of a particular product may vary as the catalyst or the particular conditions of ratios, temperatures, pressures, etc. are varied.

Reaction effluent from the reaction zone is withdrawn and passed to a fractionation operation. Here there may be obtained several principal product streams:

(i) a small amount of light ends which are produced as undesired by-products, which are withdrawn as an overhead eg from a preliminary flashing operation;

(ii) unreacted vinyl cyclohexene which may be recovered and recycled to the reaction zone;

(iii) product: aniline, styrene, and ethylbenzene; and (iv) unreacted nitrobenzene bottoms which optionally after separation from catalyst may be recycled to the reaction zone.

Clearly the particular recovery system will depend upon the composition of the reaction effluent and the preferred product to be recovered.

DESCRIPTION OF PREFERRED EMBODIMENTS

Practice of the novel process of this invention may be apparent from the following description of a preferred embodiment wherein, as elsewhere in this specification, all parts are parts by weight unless otherwise specifically noted. The accompanying drawing represents schematically a flow sheet of one technique whereby the process of this invention may be carried out. It will be apparent to those skilled in the art that the drawing may show major pieces of equipment, and that various pumps, valves, heat exchangers, collection drums, etc. may not be shown.

EXAMPLES I AND IV

In these examples, which represent a mode of carrying out the process of this invention in a batch operation, there is added to an autoclave catalyst in amount of 1.0 gram, 4-vinyl-1-cyclohexene (butadiene dimer) in amount of 16.2 grams, and nitrobenzene in amount of 12.3 grams. The autoclave is then closed and heated to reaction temperature of about 200° C. for 10 hours at autogenous pressure of about 50 psig.

At the end of the reaction period, the autoclave is cooled to ambient temperature; and the contents are analyzed to determine selectivities and yields.

EXAMPLES II-III AND V-IX

In these examples which represent a mode of carrying out the process of this invention in a continuous flow operation, the catalyst is maintained in a bed in the reaction zone; and the charge vinyl cyclohexene and nitrobenzene in liquid phase are passed through the catalyst bed. The amount of catalyst, charge vinyl cyclohexene, and charge nitrobenzene (all in grams), the temperature of reaction (°C.), the time of reaction (in hours/minutes) and the Feed Rate (in ml/min) are as set forth in Table VI. All continuous runs are carried out at 50 psig.

TABLE VI

| Example | CAT g. | Charge VCH g. | NB g. | Temp. °C. | Time Hr/Min. | Feed Ml./min |
|---|---|---|---|---|---|---|
| I[a] | 1.0 | 16.2 | 12.3 | 200-201 | 10/- | — |
| II | 3.98 | 8.1 | 6.2 | 260 | /95 | 0.154 |
| III | 4.07 | 8.1 | 6.2 | 320 | /95 | 0.147 |
| IV[a] | 1.0 | 16.2 | 12.3 | 200-202 | 10/- | — |
| V | 4.0 | 8.1 | 6.2 | 260 | /97 | 0.151 |
| VI | 3.99 | 8.1 | 6.2 | 260 | /90 | 0.161 |
| VII | 4.14 | 8.1 | 6.2 | 320 | /100 | 0.14 |
| VIII | 4.14 | 8.1 | 6.2 | 360 | /95 | 0.147 |
| IX | 4.84 | 8.1 | 6.2 | 260 | /99 | 0.147 |

[a]Autoclave runs at 50 psig

There are tabulated in Table VII for each run: the catalyst, using the letter designation from Table III; the Selectivity in mole percent for each of ethylbenzene (EB), styrene (S), and aniline (AN); and the Yield in mole % for the same components. All analyses are by Gas Chromatography.

The mole % Selectivity is:

$$\frac{\text{Moles of Product} \times 100}{\text{Moles Appropriate Starting material consumed}}$$

The mole % Yield is:

$$\frac{\text{Moles of Product} \times 100}{\text{Moles of Appropriate Starting material charged}}$$

In the case of ethylbenzene and styrene, the "Appropriate Starting material" is vinyl cyclohexene. In the case of aniline, it is nitrobenzene.

TABLE VII

| Example | Cat | Selectivity Mole % | | | Yield Mole % | | |
|---|---|---|---|---|---|---|---|
| | | EB | S | AN | EB | S | AN |
| I | A | Tr | 2.4 | 31.5 | Tr | 0.26 | 11.8 |
| II | A | 9.35 | 9.53 | 8.9 | 0.6 | 0.6 | 2.6 |
| III | A | 16.1 | 3.5 | 24.4 | 4.2 | 0.9 | 10.3 |
| IV | B | Tr | 1.73 | 19.0 | Tr | 0.13 | 12.7 |
| V | E | 23.6 | 3.4 | 9.5 | 3.5 | 0.5 | 3.0 |
| VI | C | 9.4 | 11.5 | 12.3 | 1.3 | 1.6 | 3.9 |
| VII | C | 20.6 | 3.1 | 19.2 | 4.4 | 0.7 | 9.2 |
| VIII | C | 9.9 | 1.9 | 12.5 | 3.4 | 0.6 | 6.2 |
| IX | D | 18.7 | 4.78 | 19.9 | 4.0 | 1.0 | 6.0 |

From the above illustrative data, the following conclusions may be drawn:

(i) all the examples permit attainment of desired product;

(ii) greatest selectivity to aniline (31.5%) at high yield (11.8%) is attained (Example I) at 200° C. by use, as catalyst, of 0.5% platinum and 5% Cu$_2$O on alumina in a batch operation;

(iii) Comparison of Examples II and III shows that in continuous operation, higher Selectivity and Yield of aniline are achieved at 320° C. than at 260° C.;

(iv) Example IV, using a different catalyst than Examples I-III, shows that it is possible to prepare product aniline containing very little ethylbenzene or styrene;

(v) Example V shows that it is possible to control the reaction to permit attainment of high selectivity to ethylbenzene.

Results comparable to those attained in Examples I-IX may be attained if the nitrocompound is:

| Example | R'NO$_2$ |
|---|---|
| X | dinitrobenzene |
| XI | p-nitrotoluene |
| XII | 2,4-dinitrotoluene |
| XIII | p-nitrochlorobenzene |
| XIV | 1-nitropropane |
| XV | nitrocyclohexane |

Comparable results may be attained if the catalyst is:

| Example | | Catalyst |
|---|---|---|
| XVI | 0.5% | Pt |
| | 5% | Cu$_2$O |
| | | SiO$_2$ |
| XVII | 0.4% | Rh |
| | 3% | Cu$_2$O |
| | | Al$_2$O$_3$ |
| XVIII | 0.5% | Pt |
| | 6% | Ag$_2$O |
| | | Al$_2$O$_3$ |
| XIX | 0.8% | Pd |
| | 5% | Au$_2$O |
| | | Al$_2$O$_3$ |
| XX | 1% | Pt |
| | 5% | Cu$_2$O |
| | 4% | MoO$_3$ |
| | | Al$_2$O$_3$ |
| XXI | 1% | Ir |
| | 4% | Ag$_2$O |
| | 3% | WO$_2$ |
| | | SiO$_2$ |

EXAMPLE XXII

The process of this invention may be carried out continuously in accordance with the schematic flow sheet shown in the drawing.

In this embodiment, there is admitted through line 10 charge 4-vinyl-1-cyclohexene (676.4 parts) which is combined with 143.3 parts of recycle VCH from line 11. Charge nitrobenzene (284.7 parts) is added through line 12 together with 337.9 parts of recycle NB through line 13 to total 622.6 parts total charge NB. Catalyst in a bed in operation 17 is 0.5% platinum and 5% cuprous oxide on 3 mesh gamma alumina particles.

Charge containing VCH and NB is passed through line 15 and heated in heat exchanger 16 to ca. 200° C./50 psig. The mixture is passed through reaction zone 17 at LHSV of 1.5. Reaction effluent in line 18 is flashed in flash drum 19 to yield 2.3 parts of light ends withdrawn through line 36. Flashed liquid is passed through line 20 to fractionator 21 from which overhead may be withdrawn containing 143.3 parts VCH and 50.7 parts of EB. This fractionator overhead is passed through line 22 and heat exchanger 23 to VCH tower 24 from which 143.3 parts VCH is recovered and recycled through line 11. Bottoms from VCH tower 24 include 50.7 parts EB recovered through line 25.

Bottoms from fractionator 21 containing styrene, aniline, and nitrobenzene are passed through line 26 and heat exchanger 27 to distillation tower 28 from which there are recovered through line 13 bottoms containing nitrobenzene. This stream, containing 337.9 parts of nitrobenzene, is recycled to charge through line 13.

Overhead from distillation tower 28 containing 31.5 parts of styrene and 100 parts of aniline are passed through line 32 and heat exchanger 33 to rectification tower 34. Here 31.5 parts of styrene are recovered as overhead in line 37 and 100 parts of aniline are recovered as overhead in line 37 and 100 parts of aniline are recovered as bottoms in line 38.

Although this invention has been illustrated by reference to specific embodiments, it will be apparent to those skilled in the art that various changes and modifications may be made which clearly fall within the scope of this invention.

We claim:

1. The method which comprises
    passing a charge stream containing vinyl cyclohexene and R'NO$_2$, wherein R' is alkyl, cycloalkyl, aryl, aralkyl, or alkaryl, into contact at hydrogen transfer conditions with a supported catalyst bearing (i) a Group VIII noble metal and, per mole of Group VIII noble metal, (ii) 1–20 moles of Group I B metal, present as oxide, and (iii) 0–20 moles of Group VI B metal present as oxide, thereby forming a product stream containing R'NH$_2$; and recovering said product stream containing R'NH$_2$.

2. The method as claimed in claim 1 wherein said hydrogen transfer conditions include temperature of about 170° C.–360° C. and pressure of about 0–500 psig.

3. The method as claimed in claim 1 wherein said vinyl cyclohexene is 4-vinyl-1-cyclohexene.

4. The method as claimed in claim 1 wherein said R'NO$_2$ is nitrobenzene.

5. The method as claimed in claim 1 wherein said Group VIII noble metal is platinum or palladium.

6. The method as claimed in claim 1 wherein said Group I B metal is copper, present as Cu$_2$O.

7. The method as claimed in claim 1 wherein said Group VI B metal is chromium, present as Cr$_2$O$_3$.

8. The method as claimed in claim 1 wherein said supported catalyst bears a composition consisting essentially of (i) a Group VIII noble metal and (ii) per mole of Group VIII Metal 1–20 moles of Group I B metal.

9. The method as claimed in claim 1 wherein said catalyst bears (i) platinum or palladium and (ii) copper, as Cu$_2$O, on a support.

10. The method as claimed in claim 1 wherein said catalyst bears (i) platinum or palladium, (ii) copper, as Cu$_2$O, and (iii) chromium, present as Cr$_2$O$_3$, on a support.

11. The method which comprises
    passing vinyl cyclohexene and nitrobenzene into contact at hydrogen transfer conditions, including temperature of about 170° C.–360° C. and pressure of about 0–500 psig, with a supported catalyst bearing (i) platinum or palladium as Group VIII metal, and per mole of Group VIII metal (ii) 1–20 moles of copper, present as Cu$_2$O, and (iii) 0–20 moles of chromium, as Group VI B metal, present as Cr$_2$O$_3$, thereby forming a product stream containing aniline; and recovering said product stream containing aniline.

12. A novel supported catalyst consisting essentially of
    (i) a Group VIII noble metal; and per mole of Group VIII noble metal;
    (ii) 1–20 moles of Group I B metal, present as oxide; and
    (iii) 0–20 moles of Group VI B metal present as oxide.

13. A novel supported catalyst as claimed in claim 12 wherein said Group VIII noble metal is platinum or palladium.

14. A novel supported catalyst as claimed in claim 12 wherein said Group VIII noble metal is platinum.

15. A novel supported catalyst as claimed in claim 12 wherein said Group I B metal is copper.

16. A novel supported catalyst as claimed in claim 12 wherein said Group I B metal is copper, present as Cu$_2$O.

17. A novel supported catalyst as claimed in claim 12 wherein said Group VI B metal is chromium, present as Cr$_2$O$_3$.

18. A novel supported catalyst consisting essentially of
    (i) platinum or palladium as Group VIII metal; and per mole of Group VIII metal;
    (ii) 1–20 moles of copper, present as Cu$_2$O; and
    (iii) 0–20 moles of chromium, present as Cr$_2$O$_3$.

* * * * *